(12) United States Patent
Zamar

(10) Patent No.: US 6,416,461 B1
(45) Date of Patent: Jul. 9, 2002

(54) PENILE RING

(76) Inventor: Antonios Camille Zamar, 5 Convent Close, Beckenham, Kent BR3 5GD (GB)

(*) Notice: Subject to any disclaimer, the term of this patent is extended or adjusted under 35 U.S.C. 154(b) by 0 days.

(21) Appl. No.: 09/600,188
(22) PCT Filed: Jan. 20, 1999
(86) PCT No.: PCT/GB99/00181
§ 371 (c)(1), (2), (4) Date: Jul. 12, 2000
(87) PCT Pub. No.: WO99/36008
PCT Pub. Date: Jul. 22, 1999

(30) Foreign Application Priority Data

Jan. 20, 1998 (GB) .............................................. 9801170

(51) Int. Cl.[7] .................................................. A61F 5/00
(52) U.S. Cl. .......................................... 600/41; 600/39
(58) Field of Search ...................................... 600/38–41

(56) References Cited

U.S. PATENT DOCUMENTS

| 1,615,945 A | 2/1927 | James |
| 3,939,827 A | 2/1976 | Brunstetter |
| 5,433,694 A | * 7/1995 | Lim ............................ 600/38 |

FOREIGN PATENT DOCUMENTS

| DE | 520557 | 3/1931 | |
| DE | 1942584 | 2/1971 | |
| FR | 2566265 A | * 6/1984 | ............. A61F/5/41 |

OTHER PUBLICATIONS

Nawty Things Adult Toys and Gifts; Nov. 5, 2001; http://nawtythings.com/toys/se1425_00html.*

Nawty Things Adult Toys and Gifts; Nov. 5, 2001; http://nawtythings.com/toys/se1605_00html.*

* cited by examiner

Primary Examiner—Eric F. Winakur
Assistant Examiner—Nikita R Veniaminov
(74) Attorney, Agent, or Firm—Guy McClung

(57) ABSTRACT

A device for preventing or reducing premature ejaculation in men comprises a ring, which fits around the penis with a triangular shaped desensitizing strip which is held against the penis and which has a beaded surface in contact with the penis. The device is worn and results in desensitization.

20 Claims, 4 Drawing Sheets

PENILE RING

BACKGROUND OF THE INVENTION

The present invention relates to a device which is an aid for dealing with premature ejaculation in men. Premature ejaculation is a problem which is encountered in psycho-sexual clinics and results in the man reaching orgasm and ejaculating before or immediately after penetration.

DESCRIPTION OF THE RELATED ART

There are various treatments which have been tried with varying effectiveness. One current treatment is the Squeeze (Seman Technique) in which coitus is interrupted and the glans of the penis is squeezed. This technique gives varying results and its effectiveness has been questioned and is not very satisfactory.

Drug treatments have been tried and antidepressant drugs and anti psychotic drugs have been used. These drugs are expensive to provide on a continuing basis and there can be side effects and other risks associated with taking such drugs.

I have now devised a device for assisting in overcoming premature ejaculation.

According to the invention there is provided a desensitising ring structure which comprises a ring section adapted to fit over a penis which ring section has attached to it a desensitising section which is substantially in the shape of a triangle with the base of the triangle attached to the ring section which desensitising section has a substantially smooth external surface and a substantially beaded internal surface and which, when the ring section is placed on a penis the desensitising section is held in contact with the ventral aspect of the base of the glans of the penis.

The ring can be fitted over the penis manually or by means of a suitable applicator; the applicator can be of any suitable shape or form aid the ring structure can be detachably attached to the applicator or the structure can be provided associated with the applicator The ring section can have a means to adjust its size and/or it can be stretchable to enable it to expand when it is placed on a penis.

The triangular shaped section and if flexible the ring is preferably made of a flexible material such as a plastics material, rubber or rubberised material a silicone material.

Any suitable biologically inert flexible material of the above types can be used.

The ring section can be made of any biologically inert material and can be made of the same material as the triangular shaped section. In one embodiment the ring and the triangular shaped section are made as one unit In another embodiment of the invention the triangular shaped section is attached to the ring section separately e.g. by gluing, welding etc.

By internal and external is meant with regard to the ring i.e. the internal surface of the triangular shaped section faces towards the centre of the ring and the external surface faces away from the centre of the ring so that in use the beaded section is held in contact with the base of the glans or indeed any part along the whole length of the penis.

The triangular shaped section need not be in the exact shape if a triangle e.g. it can have rounded corners etc. and the sides need not be exactly straight.

The beaded section is made so that it is bumpy i.e. it is not smooth so that it would not injure the skin of the penis but will provide stimulation when in contact with the penis. The beading can be in the form of ribs, bumps, raised sections, wavy lines etc. The aim of the stimulation is to desensitise this particularly sensitive part of the penis.

In use the ring section is placed over the penis, either manually or by means of an applicator with the apex of the triangular shaped section facing away from the base of the penis. The triangular section can be rigid or semi-rigid and it can be reinforced with other added material. In one embodiment there can be an extension which extends below the ring or band which can act as a stabiliser and can prevent the ring from turning inwards or outwards in use.

The device can be supplied separate from an applicator or with a detachable applicator. The device is worn at the base of the glans with the beaded surface in contact with the penis so that the small triangle at the anterior (ventral or lower) aspect of the penis is covered and this rubs against the beaded surface so as to desensitise this part of the glans. The device can be worn during or before intercourse and/or it can be worn for a longer period during the day or for masturbation.

If the device is to be worn during the day the ring can be made so that its width is adjustable rather than provide a tight constriction or it can be made flexible.

The device or the ring section can be actuated e.g. mechanically or electrically so that it can vibrate.

The device operates by reducing sensitisation and thus reducing the tendency to premature ejaculation.

BRIEF DESCRIPTION OF THE SEVERAL VIEWS OF THE DRAWING(S)

The device is illustrated in the accompanying drawings in which.

DETAILED DESCRIPTION OF THE INVENTION

Figure 1:
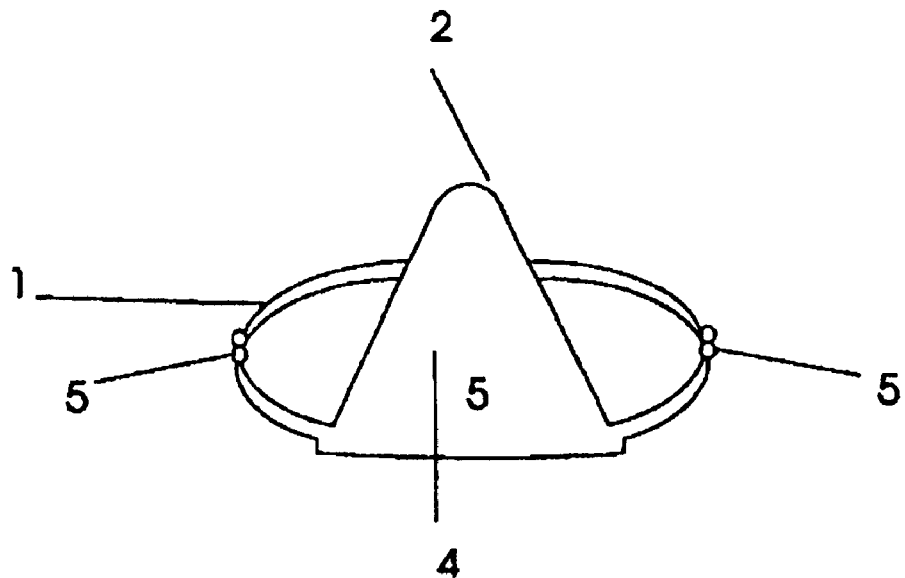
FIG. 1 is a view of the outside of the device
Figure 2:
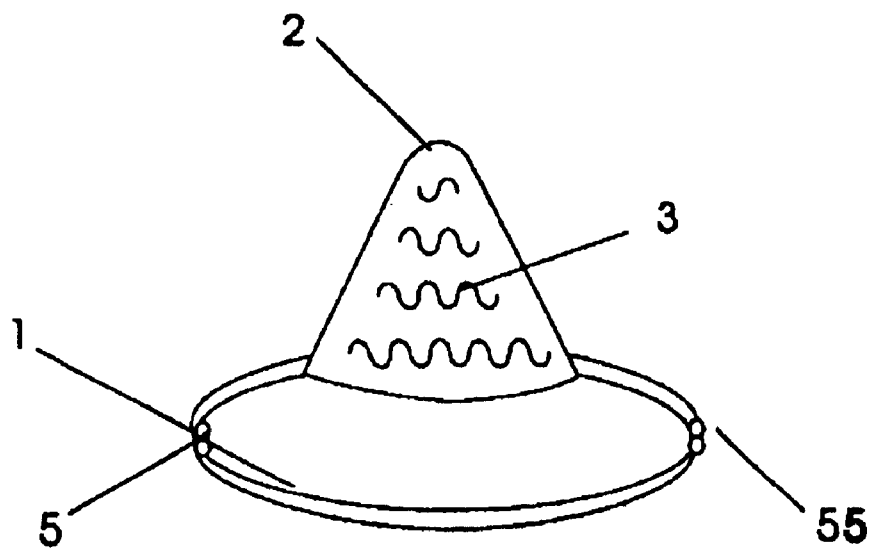
FIG. 2 is a view of the inside of the device

The device comprises a ring section (1) made of flexible, stretchable material which has attached to it a triangular shaped desensitising section (2). The inside surface of (2) is beaded or bumpy (3) and the outside surface (4) is smooth. In FIG. (3) an embodiment is illustrated in which there is a size adjustment means (5) such as a "Velcro" (RTM) join or a buckle /pin mechanism so that the size of the ring an be adjusted.

Figure 3:
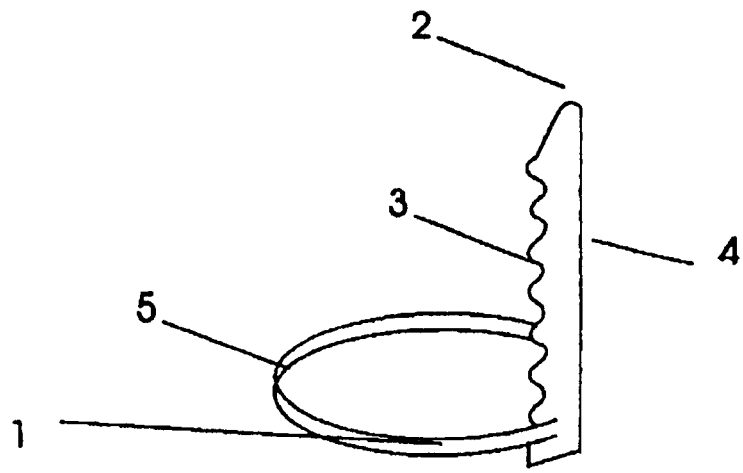
FIG. 3 is a side view of the device.
Figure 4:
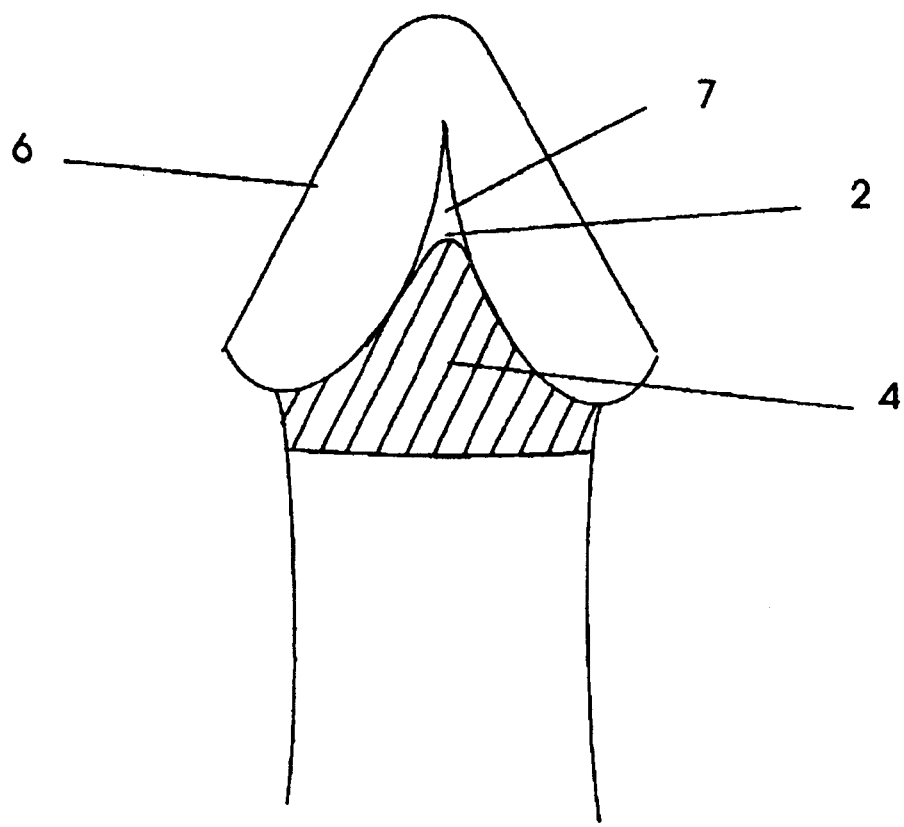
FIG. 4 is a view of the device in use

Referring to FIGS. 3 and 4, in use the ring is placed over a penis (6) with the triangular shaped section (2) fitting into the small triangle (7) at the anterior (ventral or lower) aspect of the penis with the beaded surface (3) in contact with the glans and the outside surface (4) facing outwards. Optionally there can be a thickening of the ring or a protrusion in order to facilitate holding or gripping the flexible ring.

Figure 5:
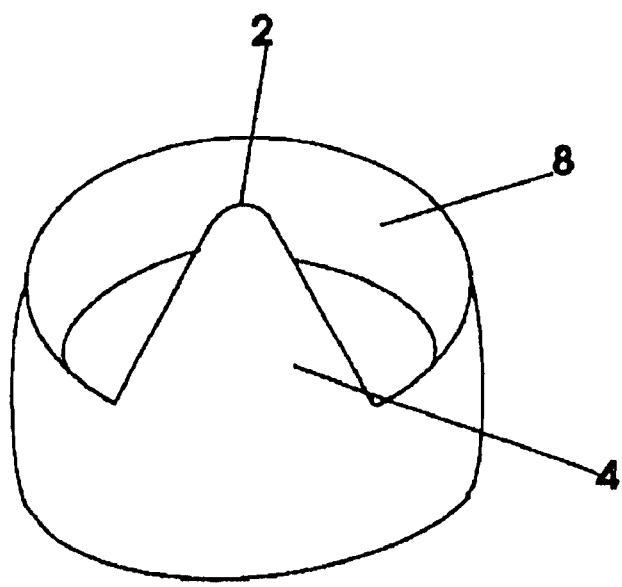
FIGS. 5 and 6 are views of a device in which the ring can extend for a longer distance and FIGS. 6 and 7 are views of a further embodiment of the invention
Figure 6:
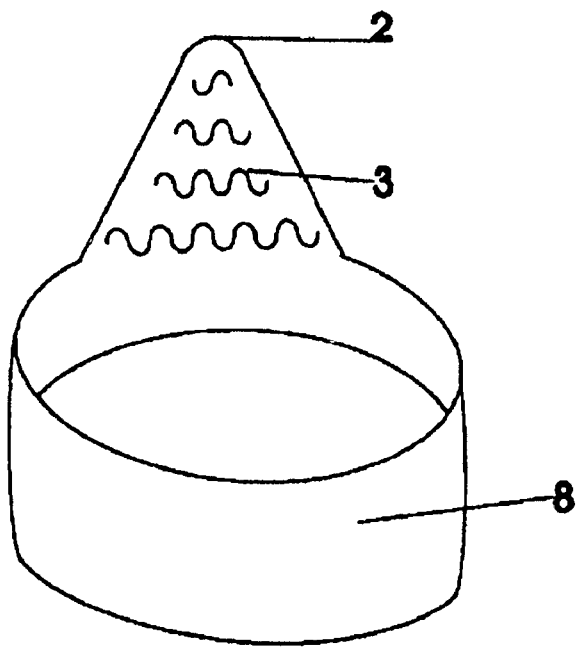

In the embodiment of FIGS. 5 and 6 the band (8) device can extend a longer distance along the penis.

Figure 7:
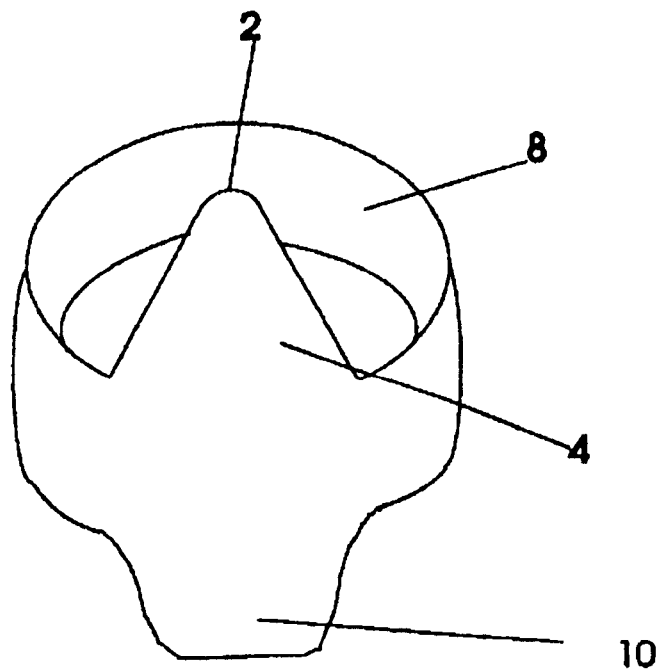
Figure 8:
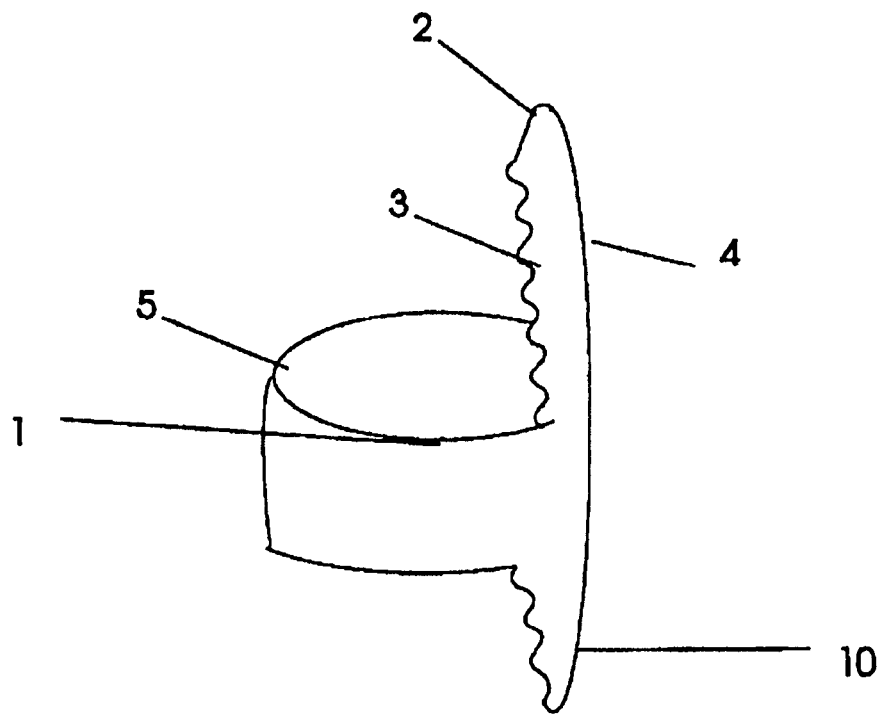

Referring to FIGS. 7 and 8, there is an extension (10) which extends downwards from the ring or band (1) and which in use helps to stailise the device and prevents the ring from turning inwards or outwards.

The device of the invention tends to de-sensitise the penis and reduce the tendency to premature ejaculation.

What is claimed:

1. A desensitising ring structure which comprises a ring section adapted to fit over a penis which ring section has attached to it a desensitising section which is substantially in the shape of a triangle with the base of the triangle attached to the ring section which desensitising section has a substantially smooth external surface and a substantially beaded internal surface and which, when the ring section is placed on a penis the desensitising section is held in contact with the ventral aspect of the base of the glans of the penis.

2. A ring structure as claimed in claim 1 in which there is an adjustment means which can adjust the size of the ring section.

3. A ring structure as claimed in claim 2 in which the triangular shaped desensitising section is made of a biologically inert flexible material.

4. A ring structure as claimed in claim 1 in which the ring section extends at least part or whole of the distance from the base of the glans to the whole length of the penis.

5. A ring structure as claimed in claim 3 in which the ring section and the desensitising section are made as one unit.

6. A ring structure as claimed in claim 5 in which the desensitising section is attached to the ring separately.

7. A ring structure as claimed in claim 4 in which the beading is in the form of ribs, bumps, straight, wavy or zigzag lines or other raised section.

8. A structure as claimed in claim 4 in which there is a stabilising extension which extends downwards from the ring in a direction substantially opposite to the direction of the triangular section, which stabilising section tends to prevent the ring from turning inwards or outwards during use.

9. A ring structure as claimed in claim 1 in which the triangular shaped desensitising section is made of a biologically inert flexible material.

10. A ring structure as claimed in claim 1 in which the ring section and the desensitising section are made as one unit.

11. A ring structure as claimed in claim 1 in which the desensitising section is attached to the ring separately.

12. A ring structure as claimed claim 1 in which the beaded section is made so that it would not injure the skin of the penis but will provide stimulation when in contact with the penis either mechanically by rubbing or by vibrating.

13. A ring structure as claimed in claim 1 in which the beading is in the form of ribs, bumps, straight, wavy or zigzag lines or other raised section.

14. A structure as claimed in claim 13 in which there is a stabilising extension which extends downwards from the ring in a direction substantially opposite to the direction of the triangular section, which stabilising section tends to prevent the ring from turning inwards or outwards during use.

15. A structure as claimed in claim 1 in which the triangular section is rigid or semi-rigid and the ring is flexible.

16. A structure as claimed in claim 1 in which there is a stabilising extension which extends downwards from the ring in a direction substantially opposite to the direction of the triangular section, which stabilising section tends to prevent the ring from turning inwards or outwards during use.

17. A structure as claimed in claim 1 which is adapted to be fitted manually over the penis.

18. A structure as claimed in claim 1 which is adapted to be fitted over the penis by means of an applicator.

19. A ring structure as claimed in claim 18 which is detachably attached to an applicator.

20. A ring structure as claimed in claim 19 together with an applicator.

* * * * *